US00PP15295P2

(12) United States Plant Patent
Weiser

(10) Patent No.: US PP15,295 P2
(45) Date of Patent: Nov. 2, 2004

(54) PEACH TREE NAMED WEISER

(50) Latin Name: *Prunus persica*
Varietal Denomination: Weiser

(76) Inventor: M. Everett Weiser, 490 Town Hill Rd., York Springs, PA (US) 17372

( * ) Notice: Subject to any disclaimer, the term of this patent is extended or adjusted under 35 U.S.C. 154(b) by 0 days.

(21) Appl. No.: 10/696,340

(22) Filed: Oct. 29, 2003

(51) Int. Cl.[7] ..... A01H 5/00
(52) U.S. Cl. ..... Plt./198

(58) Field of Search ..... Plt./198

*Primary Examiner*—Bruce R. Campell
*Assistant Examiner*—Susan B. McCormick
(74) *Attorney, Agent, or Firm*—James A. Lucas; Driggs, Lucas, Brubaker & Hogg, Co., LPA

(57) ABSTRACT

A new and distinct variety of peach tree, named 'Weiser', originated as a limb sport on a 'Bellaire' tree. It is a midseason variety maturing five days after Loring and seven to 10 days after 'Bellaire'. The fruit has an attractive bright yellow-flesh, and is freestone, large sized, and flavorful. The surface of the fruit is uniformly attractive orange-red over a yellow background.

3 Drawing Sheets

Latin name genes and species—*Prunus persica*.
Variety name: Weiser.

BACKGROUND OF THE DISCLOSURE

This invention relates to peach trees and, more specifically, to a peach tree referred to as a variety of *Prunus persica* Batsch.

I discovered this new and unique variety of peach tree as a limb mutation on a 'Bellaire' tree (not patented) in a cultivated area near York Springs, Pa. The tree of this invention produces a fruit of attractive commercial value, ripening a week to 10 days after 'Bellaire' and five days after 'Loring' (not patented).

This new variety of peach was asexually reproduced by grafting rootstock—'Lovell' (not patented) near Aspers, Pa. and such reproduction has shown this new variety to come true in two successive generations. This propagation of the new variety by grafting under standard controlled conditions clearly discloses the continued maintenance of the characteristics described herein which distinguish this new variety from the parent variety and other related varieties of peach trees.

SUMMARY OF THE INVENTION

The new and distinctive variety of peach tree produces a yellow-fleshed, freestone fruit that is attractively colored, uniformly shaped, large, exceptionally firm and flavorful. It ripens after 'Bellaire' and 'Loring', during an advantageous harvest window for the Mid-Atlantic fruit-growing region. The fruit has a red blush that is more attractive than 'Loring' and covers a greater portion of the fruit surface than 'Bellaire'. The tree is vigorous, drought tolerant and has a regular bearing habit.

DESCRIPTION OF THE DRAWINGS

This new variety of peach tree is illustrated by the accompanying digital reproduction of photographic drawings and depicts the plant by the best possible color representation using color photography.

BOTANICAL DESCRIPTION OF THE PLANT

Figure 1:
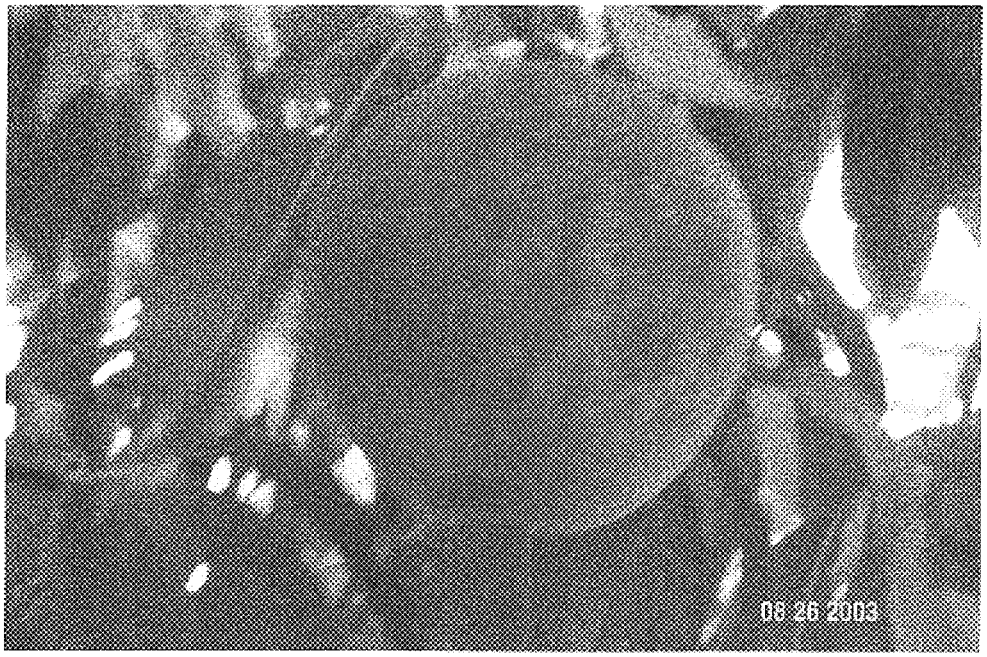
FIG. 1 is a close-up which depicts 1 specimen of fruit on the new tree, reflecting the characteristic size, shape and red blushed skin color over a contrasting yellow ground color.
Figure 2:
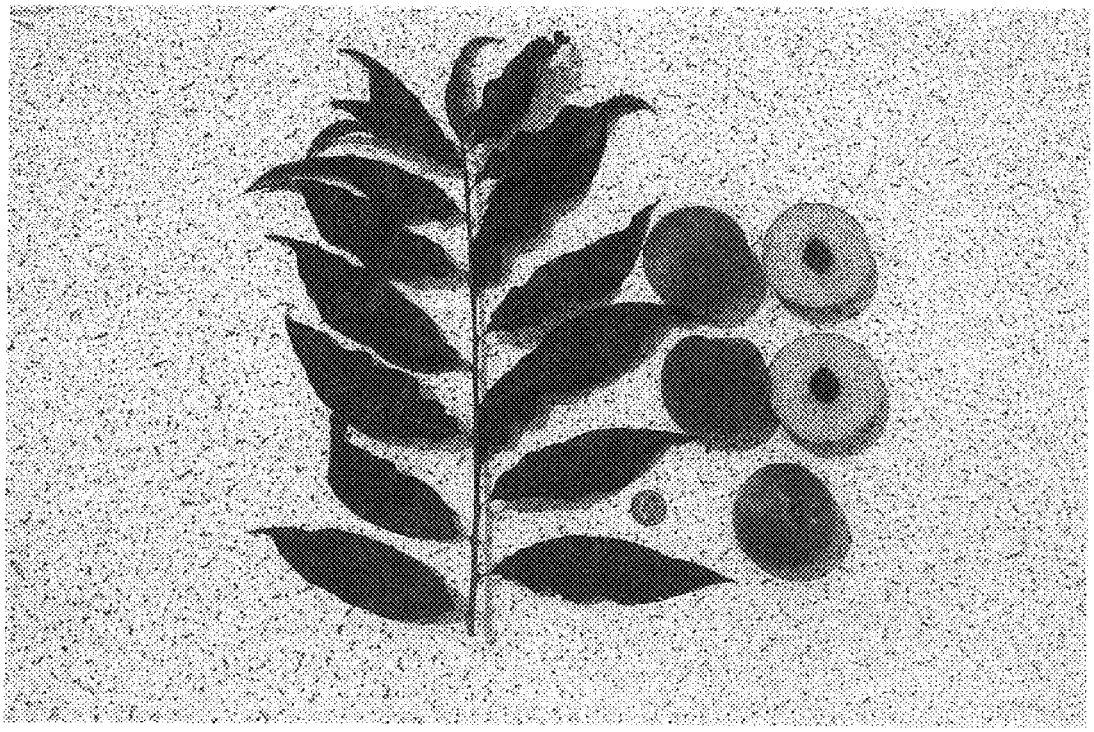
FIG. 2 depicts, at the left, a branch showing current season's growth, leaves, leaf arrangement and leaf spacing; in the middle from top to bottom, a whole specimen of a fruit shown from the apex, a whole specimen of a fruit shown from the side and a whole specimen of a fruit shown from the stem end; on the right, a partially dissected fruit.
Figure 3:
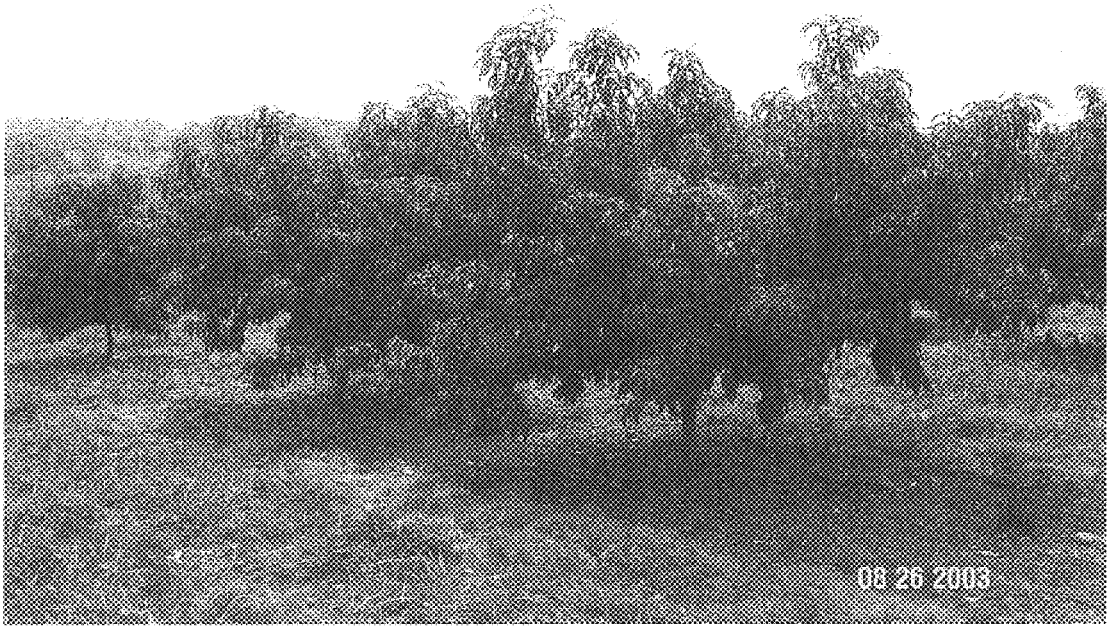
FIG. 3 shows a third generation, 4-year old tree, illustrating typical tree form, size and growth habit.

All color references below are measured against The Royal Horticultural Society (RHS) Colour Chart. Colors are approximate as color depends on horticultural practices such as light level and fertilization rate, among others.

Parentage: Limb mutation of *Prunus persica* 'Bellaire' (not patented). Asexually reproduced by bud grafting.

Tree: 2.4 m tall by 3.6 m wide at 4 years age, near York Springs, Pa.

- *Vigor.*—Similar to 'Bellaire', tolerant of drought conditions.
- *Canopy.*—Open, upright-spreading, vase tree form, 50 degree branch angle at juncture with trunk.
- *Bearing.*—Medium productive, 1 bushel per tree in 5th leaf, annual bearer, sensitivity to freeze damage similar to 'Bellaire'.
- *Trunk.*—8 cm diameter at 20 cm height from ground, medium smooth, gray-brown RHS 201C color.

Branches: 2 cm diameter, medium smooth, gray-orange RHS 177D color, medium glossy.

- *Lenticels.*—10 per $cm^2$, 2 mm long.
- *Terminal shoots.*—40 to 55 mm long.

Leaves:

- *Length.*—18 cm.
- *Width.*—3.5 to 4.5 cm.
- *Shape.*—Long oblanceolate with acuminate apex and cuneate base, thin, upward-folding, slightly undulating.

*Color.*—Olive green, RHS 137A on top surface, RHS 137B on bottom surface.

*Venation.*—Parallel, olive green RHS 137B.

*Margins.*—Crenulate.

*Petioles.*—9 to 11 mm long, 1 to 2 mm thick, olive green RHS 138B.

*Glands on petioles and base of leaves.*—0 to 4, opposite, green to brown, mostly globose, some reniform.

*Stipules.*—0 to 2, 1 to 1.5 mm long, olive green RHS 138C.

Flowers:

*Dates of first and full blossoms.*—Average April 18 and April 22 (compared to April 21 and 25 for 'Redhaven') in York Springs, Pa.

*Flowering.*—Early mid-season bloom period, blooms with 'Loring'.

*Pollination requirements.*—Self-fertile.

*Bloom density.*—Medium.

*Flower petal.*—5 per flower, orbicular shape, smooth texture, cupped, color rich pink-purple (RHS 65B) on both surfaces with tinge of RHS 66B at base, 19 mm wide, 20 mm long.

Reproductive Organs:

*Floral structures.*—Perigynous, radially symmetrical.

*Stamens.*—15 mm long, many filaments color RHS 66B, anther and pollen color RHS 11A.

*Pistil.*—Singular, 15 mm long, style color RHS 155B, stigma color RHS 1C. Ovary—one, superior, color RHS 155B.

Fruit:

*Dates of first and last pickings.*—Aug. 17 and 25 in 2003 in York Springs, Pa.

*Number of pickings.*—5.

*Maturity when described.*—Firm-ripe.

*Size.*—Uniform, medium-large (similar to 'Bellaire' and 'Loring').

*Shape and dimensions of fruit.*—Axial diameter — 6.5 to 7.5 cm.

*Transverse in suture plane.*—22 to 23 cm circumference.

*At right angles to suture plane.*—21 to 22 cm.

*Form.*—Globose to slightly oblong, symmetrical.

*Suture.*—Slightly noticeable line, continuous from stem end to apex, slight marked depressions near stem and pistil point, generally not raised.

*Ventral surface.*—Founded, lips equal.

*Cavity.*—Rounded, suture showing on one side, depth 10 to 12 mm, breadth 20 to 22 mm, no markings.

*Base.*—Rounded.

*Apex.*—Rounded to truncate.

*Stem.*—6 to 7 mm long, 4 to 5 mm wide, glabrous, medium adherence to stone.

*Skin.*—Medium thick, medium tender, free, no tendency to break.

*Color.*—Blushed or mottled orange-red, RHS 44A, covering 50 to 90% of fruit surface (compared to 30 to 40% with 'Loring'), over yellow-orange background, RHS 22C. A few stripes.

*Pubescence.*—Moderate, short, lighter than 'Loring'.

*Flesh.*—Highly attractive yellow color, RHS 13C, few red streaks except near pit, slow rate of oxidation.

*Surface of pit cavity.*—Red, RHS 47A.

*Texture.*—Firm, ~15 lbs (measured on the cheeks) at harvest.

*Fibres.*—Few, fine.

*Ripens.*—Fairly evenly.

*Flavor.*—Delicate, sub-acid, ~10% soluble solids.

*Aroma*—Mild.

*Eating quality.*—Good to best.

Stone: Free.

*Color.*—Red, RHS 47A.

*Fibres.*—Part from flesh smoothly.

*Size.*—36 mm long, 28 mm wide, 17 mm thick.

*Form.*—Oblong.

*Base.*—Oblique.

*Hilum.*—3 mm wide.

*Apex.*—Acute.

*Sides.*—Equal.

*Surface.*—Furrowed throughout, moderate number of pits.

*Ridges.*—Rounded toward apex.

*Pits.*—Circular or elongated.

Uses: Local, dessert and culinary markets. Flesh resists browning, making it ideal for canning and freezing.

Keeping quality: Excellent.

Resistance to insects: Similar to other cultivars commonly grown in the Eastern United States.

Resistance to diseases: Similar to other cultivars commonly grown in the Eastern United States.

Shipping quality: Good to excellent, equal to or better than 'Loring' and 'Bellaire'.

Chilling requirements: 800 hours.

I claim:

1. A new and distinct variety of peach tree, as illustrated and described, characterized by attractive fruit of 50 to 90% orange-red color, large size and firm, non-browning flesh.

* * * * *

08 26 2003